(12) United States Patent
Khairkhahan et al.

(10) Patent No.: US 9,205,225 B2
(45) Date of Patent: Dec. 8, 2015

(54) DELIVERY CATHETER SYSTEMS AND METHODS

(71) Applicant: Pacesetter, Inc., Sunnyvale, CA (US)

(72) Inventors: Alexander Khairkhahan, Palo Alto, CA (US); Alan Klenk, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/590,184

(22) Filed: Jan. 6, 2015

(65) Prior Publication Data

US 2015/0112361 A1    Apr. 23, 2015

Related U.S. Application Data

(62) Division of application No. 14/084,034, filed on Nov. 19, 2013, now Pat. No. 8,958,892, which is a division of application No. 13/324,781, filed on Dec. 13, 2011, now Pat. No. 8,615,310.

(60) Provisional application No. 61/422,620, filed on Dec. 13, 2010.

(51) Int. Cl.
*A61M 25/00* (2006.01)
*A61N 1/362* (2006.01)
*A61N 1/375* (2006.01)
*A61N 1/05* (2006.01)

(52) U.S. Cl.
CPC ........... *A61M 25/0074* (2013.01); *A61N 1/057* (2013.01); *A61N 1/0573* (2013.01); *A61N 1/362* (2013.01); *A61N 1/3756* (2013.01); *A61N 2001/058* (2013.01)

(58) Field of Classification Search
CPC . A61M 25/0074; A61N 1/057; A61N 1/0573; A61N 1/362; A61N 1/3756; A61N 2001/058
USPC .......................................... 607/127
See application file for complete search history.

(56) References Cited

U.S. PATENT DOCUMENTS

| | | | | |
|---|---|---|---|---|
| 8,615,310 | B2* | 12/2013 | Khairkhahan | A61N 1/3756 607/122 |
| 2010/0292541 | A1* | 11/2010 | Hashiba | A61B 17/3421 600/209 |
| 2010/0312332 | A1* | 12/2010 | Forster | A61F 2/2418 623/2.1 |

OTHER PUBLICATIONS

Notice of Allowance, U.S. Appl. No. 14/084,034, mailed Oct. 7, 2014; 12 pages.

(Continued)

*Primary Examiner* — Carl H Layno
*Assistant Examiner* — Erin Piateski
(74) *Attorney, Agent, or Firm* — Theresa A. Raymer

(57) ABSTRACT

A delivery system for implanting a leadless cardiac pacemaker into a patient is provided. The cardiac pacemaker can include a docking or delivery feature having a through-hole disposed on or near a proximal end of the pacemaker for attachment to the delivery system. In some embodiments, the delivery catheter can include first and second tethers configured to engage the delivery feature of the pacemaker. The tethers, when partially aligned, can have a cross-sectional diameter larger than the through-hole of the delivery feature, and when un-aligned, can have a cross-sectional diameter smaller than the through-hole of the delivery feature. Methods of delivering the leadless cardiac pacemaker with the delivery system are also provided.

3 Claims, 17 Drawing Sheets

(56) References Cited

OTHER PUBLICATIONS

Amendment, U.S. Appl. No. 14/084,034, filed Jul. 16, 2014, 12 pages.

Non-Final Office Action, U.S. Appl. No. 14/084,034, mailed Apr. 16, 2014, 12 pages.

Notice of Allowance, U.S. Appl. No. 13/324,781, mailed Aug. 19, 2013, 7 pages.

Amendment, U.S. Appl. No. 13/324,781, filed Jun. 12, 2013, 6 pages.

Non-Final Office Action, U.S. Appl. No. 13/324,781, mailed Mar. 29, 2013, 9 pages.

Response to Restriction Requirement, U.S. Appl. No. 13/324,781, filed Jan. 17, 2013, 7 pages.

Restriction Requirement, U.S. Appl. No. 13/324,781, mailed Dec. 17, 2012, 8 pages.

* cited by examiner

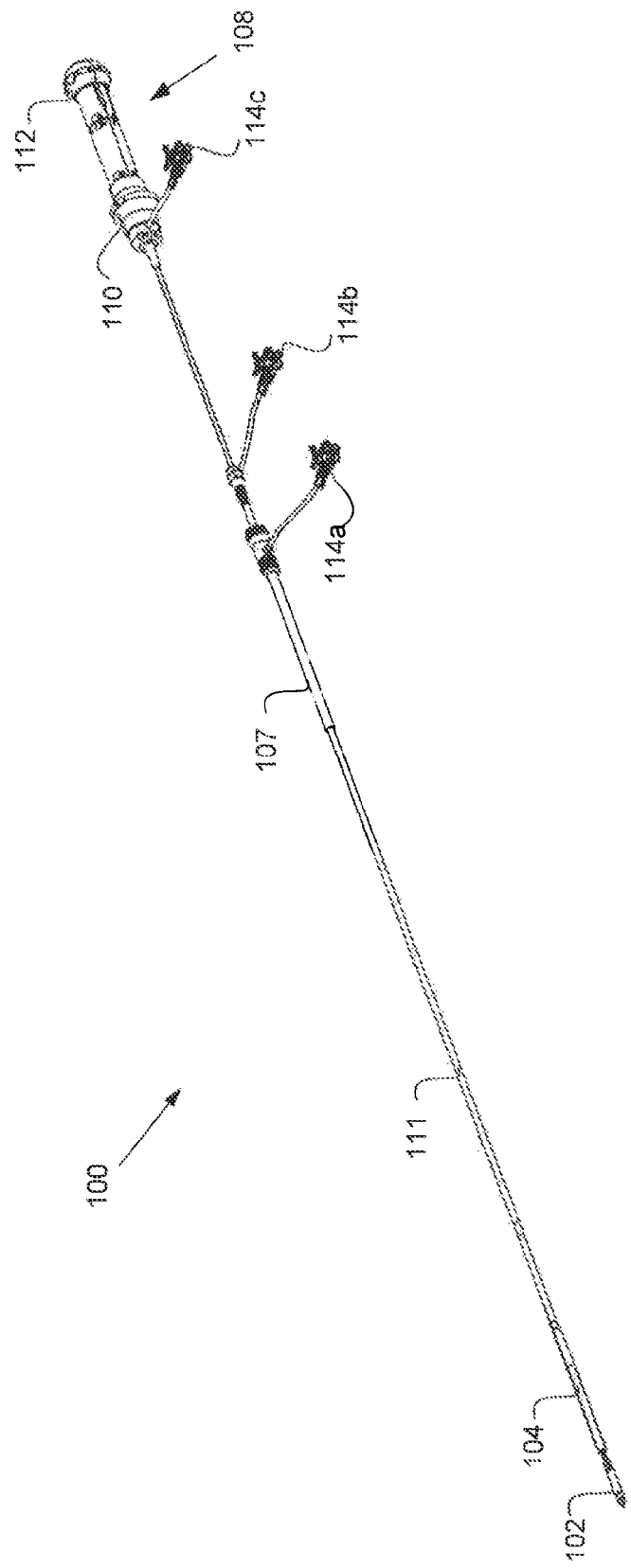

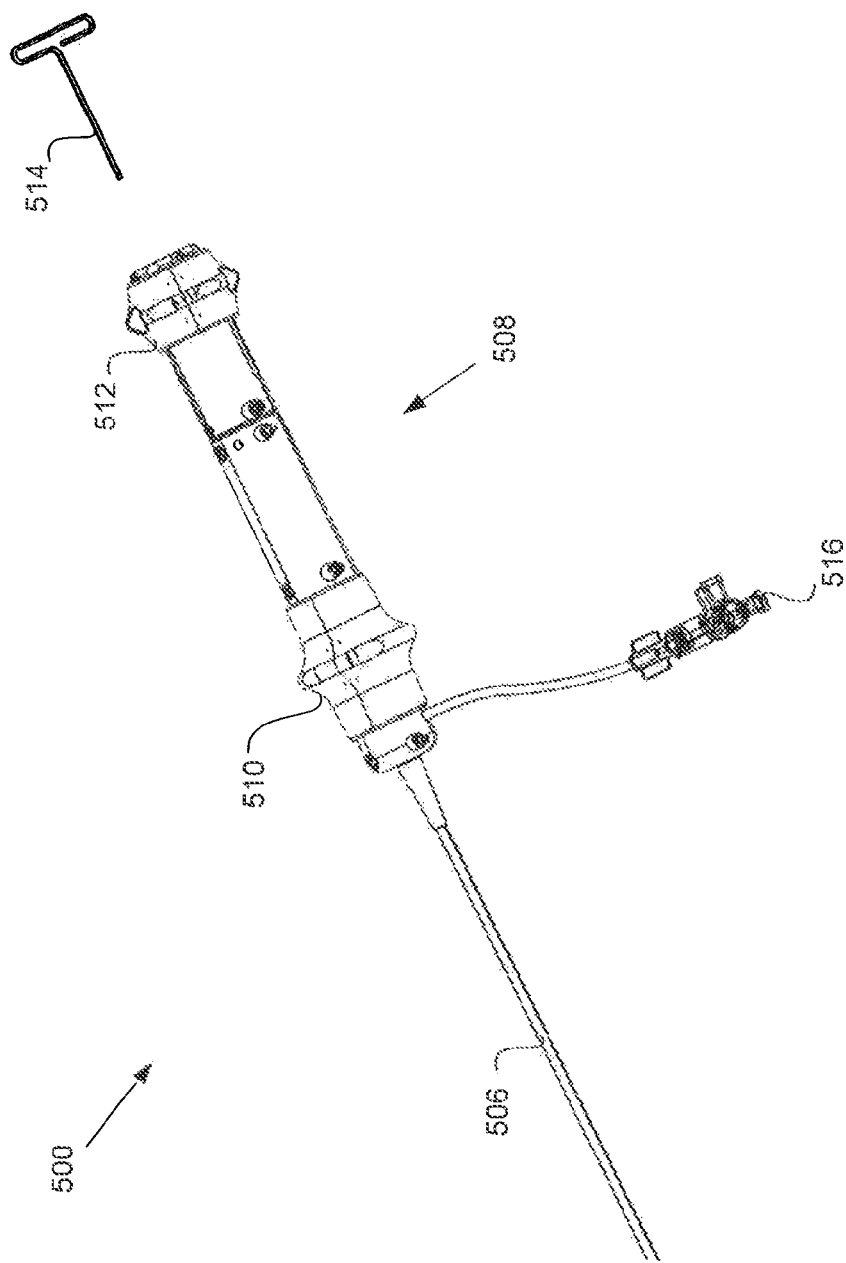

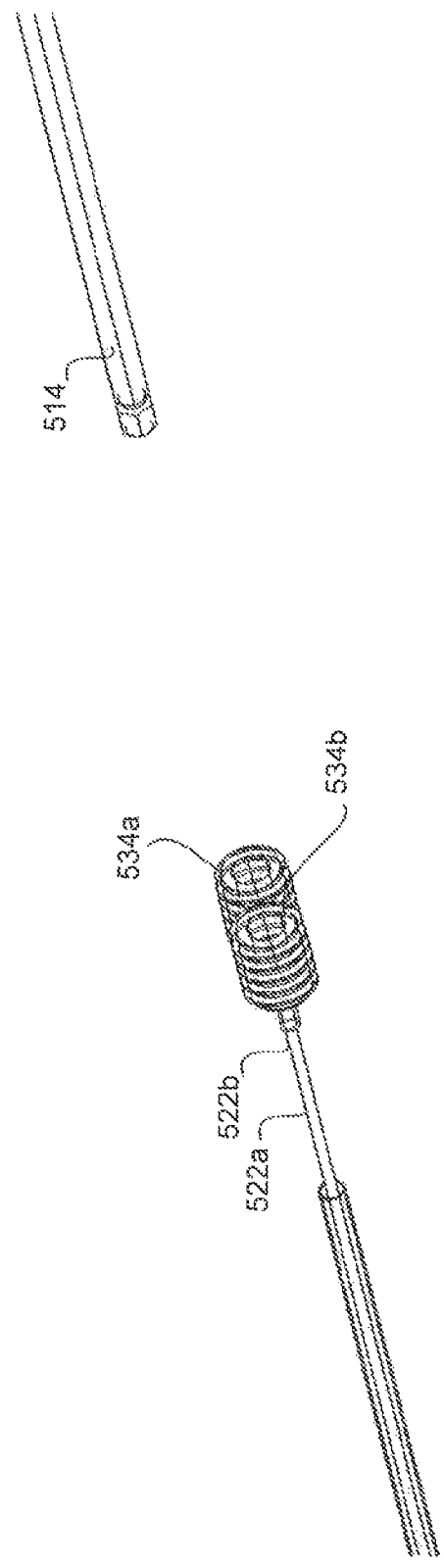

DELIVERY CATHETER SYSTEMS AND METHODS

PRIORITY CLAIM

This application is a Divisional application of U.S. patent application Ser. No. 14/084,034, filed Nov. 19, 2013, now U.S. Pat. No. 8,615,310, entitled "Delivery Catheter Systems and Methods" which is a Divisional application of U.S. patent application Ser. No. 13/324,781, filed Dec. 13, 2011, now U.S. Pat. No. 8,958,892, entitled "Delivery Catheter Systems and Methods" which claims the benefit of U.S. Provisional Patent Application No. 61/422,620, filed Dec. 13, 2010, titled "Delivery Catheter Systems and Methods." Each patent application identified above is incorporated herein by reference in its entirety to provide continuity of disclosure.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers, and more particularly, to features and methods by which they are affixed within the heart. More specifically, the present disclosure relates to features and methods for delivering a leadless cardiac pacemaker to tissue.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an actively engaging mechanism such as a screw or helical member that screws into the myocardium.

SUMMARY OF THE DISCLOSURE

In one embodiment, a delivery catheter for implanting a medical device is provided, comprising a handle, a catheter shaft coupled to the handle, a first tether disposed within the catheter shaft and extending distally beyond the catheter shaft, the first tether including a first locking feature positioned near a distal portion of the first tether, a second tether disposed within the catheter shaft and extending distally beyond the catheter shaft, the second tether including a second locking feature positioned near a distal portion of the second tether, a tether adjustment feature coupled to the first tether, the tether adjustment feature configured to adjust a length of the first tether extending distally beyond the catheter shaft.

In some embodiments, the delivery catheter comprises an aligned configuration where the first and second locking features are positioned at least partially side by side, and an un-aligned configuration where the first and second locking features are not positioned side by side.

In some embodiments, the tether adjustment feature facilitates switching the delivery catheter between the aligned configuration and the un-aligned configuration.

In one embodiment, the delivery catheter further comprises a docking cap disposed on a distal portion of the catheter shaft, and a torque shaft disposed within the catheter shaft, the torque shaft coupled to the docking cap, the torque shaft being configured to apply rotational torque to the docking cap to rotate the docking cap.

In another embodiment, the delivery catheter further comprises a protective sheath disposed on the catheter shaft, the protective sheath being slidable along the catheter shaft and comprising a crease that runs longitudinally along the protective sheath, wherein the protective sheath is configured to be folded over itself along the crease to reduce a delivery diameter of the protective sheath.

A leadless pacemaker and delivery system is also provided, comprising a leadless cardiac pacemaker comprising an attachment feature disposed on a proximal portion of the pacemaker, the attachment feature including a through-hole having a first diameter, and a delivery catheter comprising: a handle, a catheter shaft coupled to the handle, a first tether disposed within the catheter shaft and extending distally beyond the catheter shaft, the first tether including a first locking feature positioned near a distal portion of the first tether, a second tether disposed within the catheter shaft and extending distally beyond the catheter shaft, the second tether including a second locking feature positioned near a distal portion of the second tether; and a tether adjustment feature coupled to the first tether, the tether adjustment feature configured to adjust a position of the first locking feature with respect to the second locking feature, the delivery catheter comprising an aligned configuration where a portion of the first locking feature is longitudinally aligned with a portion the second locking feature and comprises a combined cross-sectional diameter larger than the first diameter of the through-hole, the delivery catheter also comprising an un-aligned configuration where the first locking feature is not longitudinally aligned with the second locking feature and comprises a combined cross-sectional diameter smaller than the first diameter of the through-hole.

In some embodiments, the tether adjustment feature facilitates switching the delivery catheter between the aligned configuration and the un-aligned configuration.

In another embodiment, the catheter can further comprise a docking cap disposed on a distal portion of the catheter shaft, and a torque shaft disposed within the catheter shaft, the torque shaft coupled to the docking cap, the torque shaft being configured to apply rotational torque to the docking cap to rotate the docking cap.

In one embodiment, the delivery catheter can further comprise a protective sheath disposed on the catheter shaft, the protective sheath being slidable along the catheter shaft and comprising a crease that runs longitudinally along the protective sheath, wherein the protective sheath is configured to be folded over itself along the crease to reduce a delivery diameter of the protective sheath.

A method of delivering a medical device to a patient with a delivery catheter is also provided, comprising positioning an attachment feature of the medical device in proximity to an attachment mechanism of the delivery catheter, inserting the attachment mechanism of the delivery catheter distally through a hole in the attachment feature of the medical device, the attachment mechanism having a cross-sectional diameter smaller than a diameter of the hole, increasing the cross-sectional diameter of the attachment mechanism to prevent the attachment mechanism from moving proximally back through the hole of the attachment feature of the medical device.

In some embodiments, the attachment feature comprises a pair of tethers disposed within and extending distally beyond the delivery catheter, each of the tethers having a locking feature.

In one embodiment, the attachment feature has a cross-sectional diameter smaller than the diameter of the hole when portions of the locking features of the tethers are not longitudinally aligned.

In another embodiment, the increasing the cross-sectional diameter step comprises longitudinally aligning at least a portion of the locking features of the tethers.

In some embodiments, the medical device comprises a leadless cardiac pacemaker.

In one embodiment, the method comprises pulling the medical device proximally with the attachment mechanism to place the medical device in contact with a distal end of the delivery catheter.

In another embodiment, the method further comprises inserting the medical device and the delivery catheter into the patient adjacent to an implantation site, and applying rotational torque from the delivery catheter to the medical device to screw a fixation device of the medical device into the implantation site.

Another method of delivering a leadless pacemaker to a patient with a delivery catheter is provided, comprising positioning a first locking feature of a first tether of the delivery catheter at a longitudinal position different than that of a second locking feature of a second tether of the delivery catheter, so that a combined cross-sectional diameter of the locking features is less than a cross-sectional diameter of a hole in an attachment feature of the leadless pacemaker, inserting the first and second locking features through the hole in the attachment feature of the leadless pacemaker, and aligning a portion of the first locking feature at the same longitudinal position than that of a portion of the second locking feature, so that the combined cross-sectional diameter of the locking features and tethers is greater than the cross-sectional diameter of the hole in the attachment feature of the leadless pacemaker.

In some embodiments, the method further comprises pulling the medical device proximally with the first and second tethers to place the leadless pacemaker in contact with a distal end of the delivery catheter.

In another embodiment, the method further comprises inserting the medical device and the delivery catheter into the patient adjacent to an implantation site, and applying rotational torque from the delivery catheter to the leadless pacemaker to screw a fixation device of the pacemaker into the implantation site.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is one embodiment of a delivery system for delivering a leadless pacemaker.

FIGS. 5A-5D are various views of a catheter handle and tether key.

DETAILED DESCRIPTION

Figure 2A:
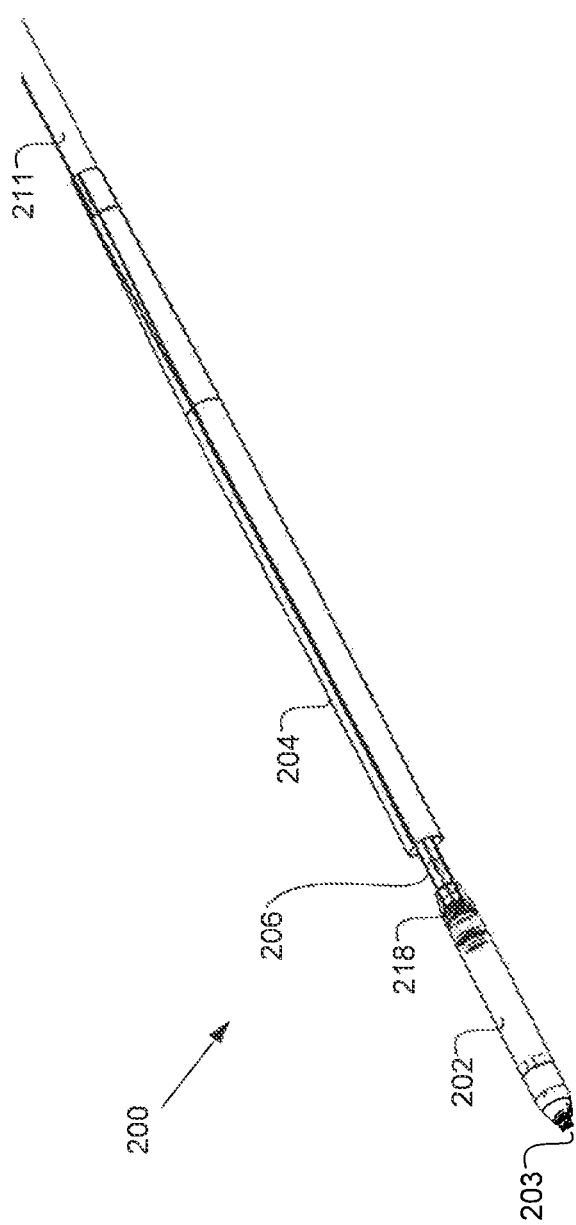
FIGS. 2A-2B are close-up views of a distal portion of the delivery system.

Various embodiments for delivering system comprising one or more leadless cardiac pacemakers or biostimulators are described. A leadless cardiac pacemaker can communicate by conducted communication, representing a substantial departure from conventional pacing systems. For example, an illustrative cardiac pacing system can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

An embodiment of a cardiac pacing system configured to attain these characteristics comprises a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism or primary fixation mechanism such as a screw or helical member that screws into the myocardium. Examples of such leadless biostimulators are described in the following publications, the disclosures of which are incorporated by reference: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. application Ser. No. 11/549,596 filed on Oct. 13, 2006, entitled "Leadless Cardiac Pacemaker Triggered by Conductive Communication" and published as US2007/0088398A1 on Apr. 19, 2007; (5) U.S. application Ser. No. 11/549,603 filed on Oct. 13, 2006, entitled "Rate Responsive Leadless Cardiac Pacemaker" and published as US2007/0088400A1 on Apr. 19, 2007; (6) U.S. application Ser. No. 11/549,605 filed on Oct. 13, 2006, entitled "Programmer for Biostimulator System" and published as US2007/0088405A1 on Apr. 19, 2007; (7) U.S. application Ser. No. 11/549,574, filed on Oct. 13, 2006, entitled "Delivery System for Implantable Biostimulator" and published as US2007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some biostimulators may further include a secondary fixation mechanism to provide another feature for keeping the biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the biostimulator from moving around in the body in the case of accidental detachment). Further details on secondary fixation mechanisms can be found in U.S. application Ser. No. 12/698,969.

Leadless pacemakers or biostimulators can be delivered to and retrieved from a patient using any of the delivery systems described herein. In some embodiments, a biostimulator is attached or connected to a delivery system and advanced intravenously into the heart. The delivery system can include features to engage the biostimulator to allow fixation of the biostimulator to tissue. For example, in embodiments where the biostimulator includes an active engaging mechanism, such as a screw or helical member, the delivery system can include a docking cap or key configured to engage the biostimulator and apply torque to screw the active engaging mechanism into the tissue. In other embodiments, the delivery system includes clips designed to match the shape of a feature on the biostimulator and apply torque to screw the active engaging mechanism into the tissue.

FIG. 1 illustrates a pacemaker delivery system 100 configured for delivery of a leadless pacemaker 102 into a patient. The delivery system 100 can include pacemaker sheath 104, guide catheter shaft 111, pacemaker introducer sheath 107, handle 108, deflection knob 110, tether shuttle 112, and flush ports 114a, 114b, and 114c The deflection knob 110 can be used to steer and guide the catheter during implantation and/or removal of the pacemaker. The flush ports 114a, 114b, and 114c can be used to flush saline or other fluids through the catheter. Sheath 107 can be advanced distally over catheter shaft 111 to provide additional steering and support for the delivery catheter during implantation and to surround the pacemaker as it is introduced through a trocar or introducer into the patient.

Figure 2B:
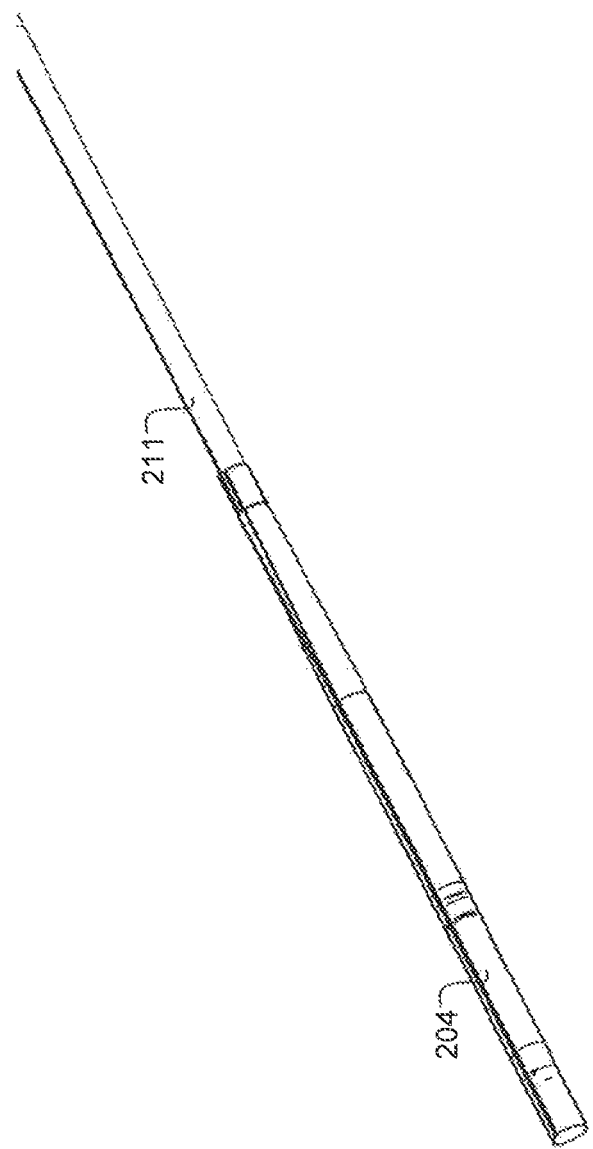

FIG. 2A is a close-up view of a distal portion of delivery system 200 and pacemaker 202. The pacemaker of FIG. 2A can include a helix 203 for attachment of the pacemaker to tissue. In FIG. 2A, the pacemaker is attached to docking cap 218 of catheter shaft 206. Pacemaker sheath 204 is shown pulled back proximally along catheter shaft 206 and guide catheter shaft 211 to expose the pacemaker 202 and helix 203. In FIG. 2B, pacemaker sheath 204 is extended distally along guide catheter shaft 211 to cover the catheter shaft 206, pacemaker 202, and helix to protect the tissue from the sharp edges of the helix during implantation. When the pacemaker sheath is pulled back proximally, as shown in FIG. 2A, the pacemaker 202 is in an exposed, delivery configuration. When the pacemaker sheath is advanced distally to protect the pacemaker and helix, as shown in FIG. 2B, the pacemaker 202 is in a protected, advancement configuration.

Figure 3A:
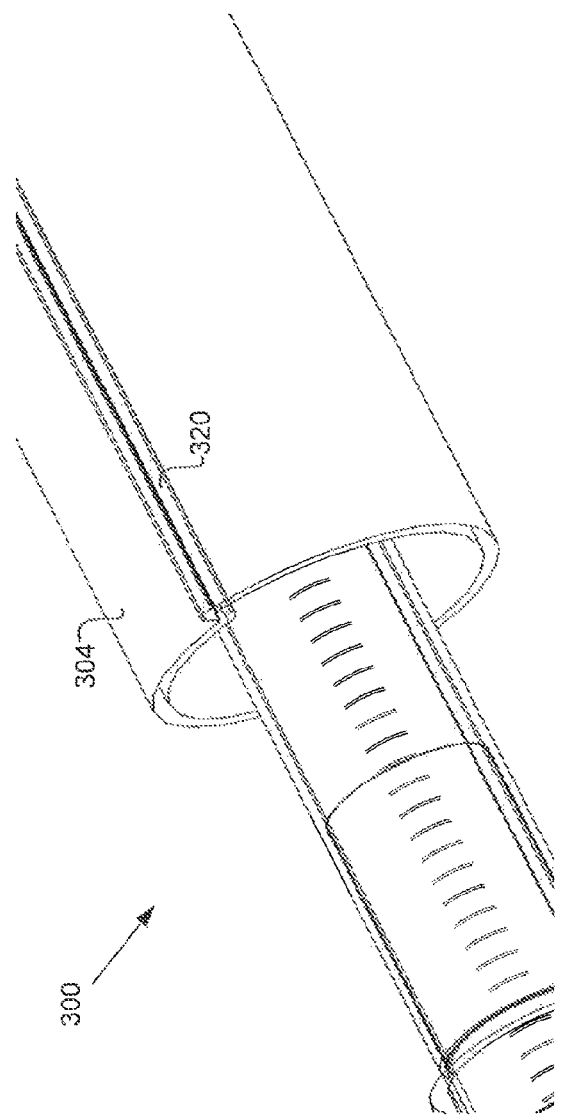
FIGS. 3A-3B are schematic side and cross-sectional views of a pacemaker sheath.
Figure 3B:
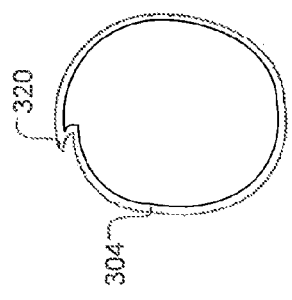

FIGS. 3A-3B are close-up and cross sectional views of pacemaker sheath 304 of delivery system 300. As shown, pacemaker sheath 304 can include crease or fold 320 along the length of the sheath. During initial insertion of the delivery system into a patient, a physician can gain access to the patient's venous system with an introducer sheath using the Seldinger technique (not shown). The delivery system, including the leadless pacemaker and catheter shaft, can then be advanced through the introducer sheath into the patient's venous system to facilitate delivery of the pacemaker into the heart. Reducing the diameter of the pacemaker, the delivery system, and thus the introducer sheath, provides for easier and less intrusive access to a patient's venous system.

By designing pacemaker sheath 304 with a fold 320 that runs longitudinally along the sheath, the cross sectional diameter of the pacemaker sheath can be reduced by folding the sheath over itself. Thus, during initial implantation of the pacemaker through a introducer sheath into the patient, the pacemaker sheath can be positioned just proximally to the pacemaker, and folded along fold 320 so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized pacemaker sheath. After the delivery system is inserted through the introducer sheath into the patient, the sheath can be advanced distally over the leadless pacemaker. Advancing the pacemaker sheath distally causes fold 320 to unfold thereby increasing the diameter of the pacemaker sheath so that it can slide over and cover the pacemaker and fixation helix. FIG. 3B is a cross sectional view of the pacemaker helix 304 and fold 320, giving another view on how the cross sectional diameter of the pacemaker sheath can increase and decrease.

Figure 4A:
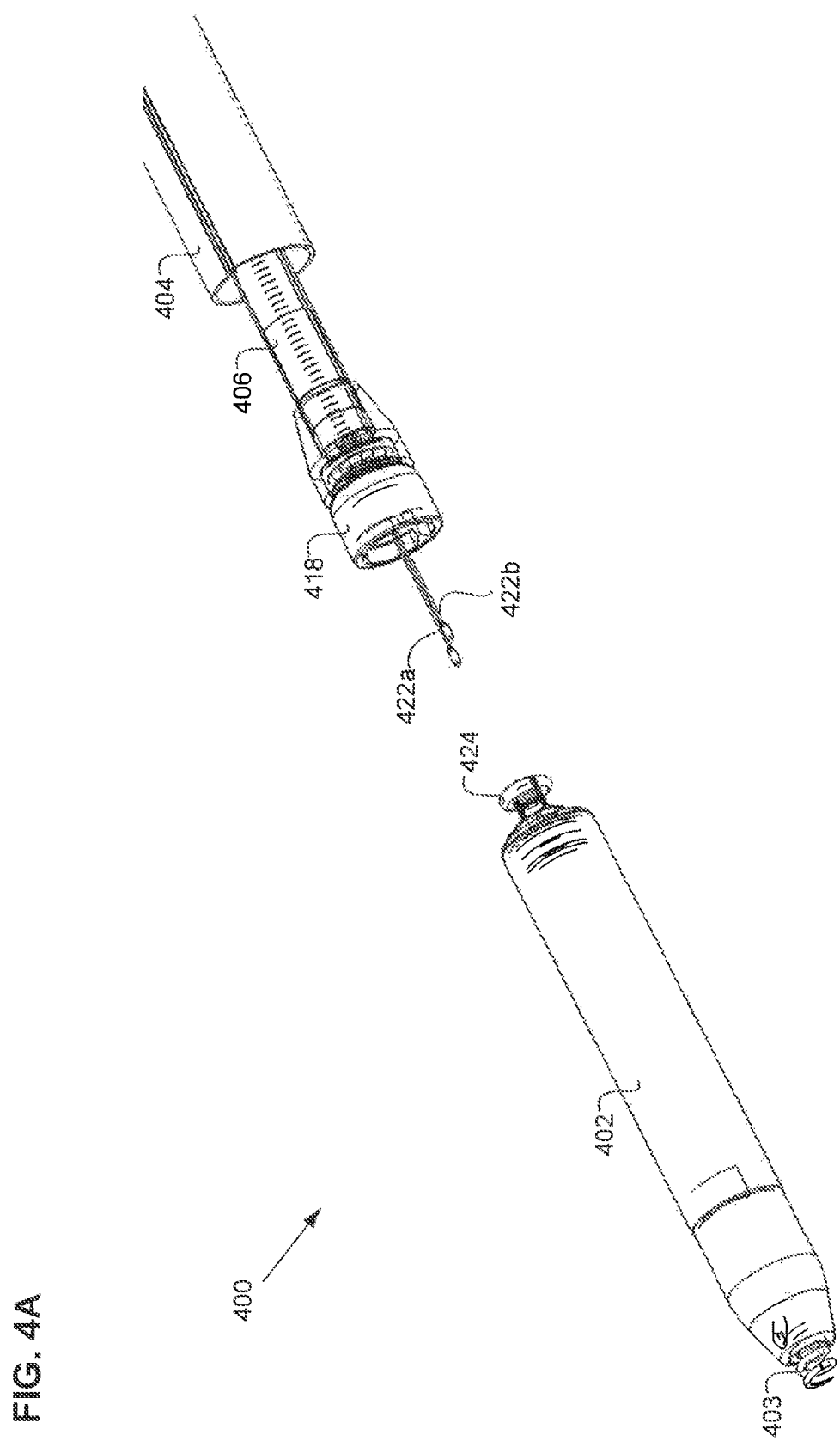
FIGS. 4A-4G are side views of a delivery system attached to a pacemaker.

FIG. 4A illustrates delivery system 400, including pacemaker 402 comprising helix 403 and attachment feature 424, and the delivery catheter comprising pacemaker sheath 404, catheter shaft 406, docking cap 418, and tethers 422a and 422b. The tethers can comprise wires, shafts, tubes, cords, ropes, strings, or other similar structures that can extend throughout the catheter shaft. In some embodiments, the tethers comprise a shape memory material, such as nitinol. In other embodiments, the tethers comprise stainless steel wires or braids. In FIG. 4A, the pacemaker 402 is not attached to docking cap 418 of the delivery catheter. The process of connecting the pacemaker to the delivery catheter will now be described.

Figure 4B:
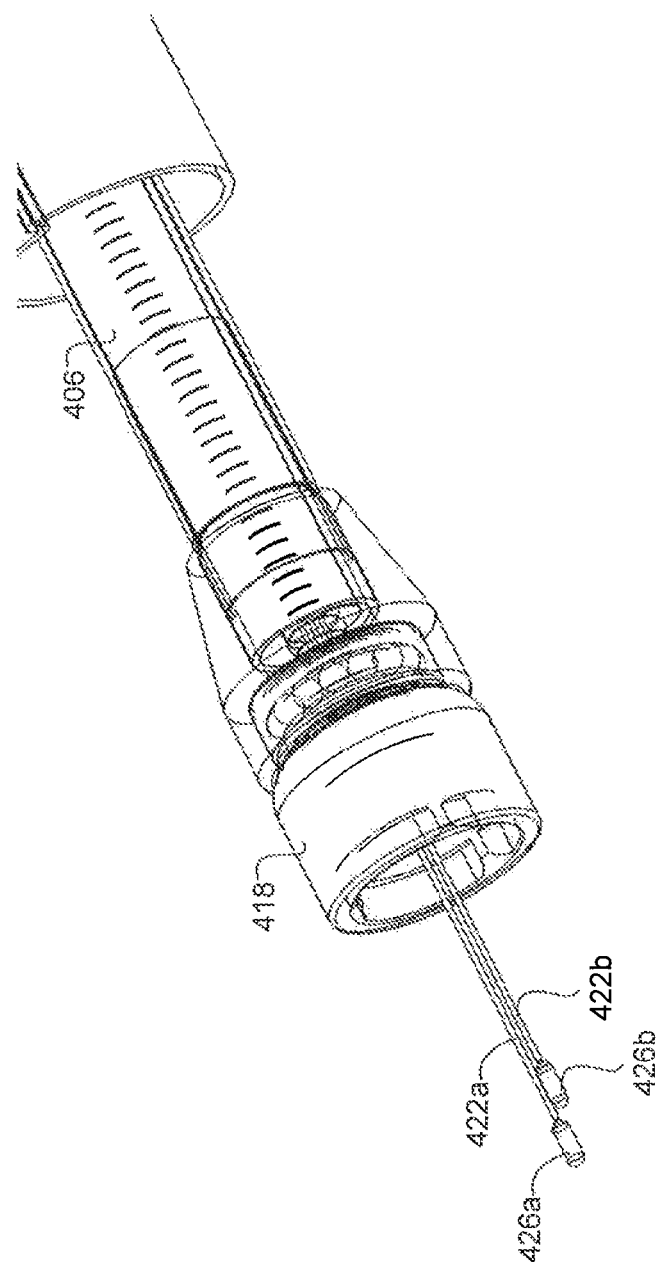

Referring to FIG. 4B, tethers 422a and 422b can include distal features 426a and 426b. The distal features can be, for example, features on the tethers that protrude radially from the tether, such as bumps, spheres, cylinders, rectangles, or other similar shapes extending outwards from the tethers. In some embodiments, the distal features can be expandable, such as balloons or expandable mechanical structures. Generally, the distal features have a cross sectional diameter larger than the cross sectional diameter of the tethers. As shown, in one embodiment, distal feature 422a can be advanced further from the catheter than distal feature 422b, so that when the tethers are pushed together, distal feature 422b rests against tether 422a. This causes the combined cross sectional diameter of both distal features and tethers to be less than if the distal features were lined up side by side. By way of comparison, in FIG. 4C the distal features 426a and 426b are lined up side by side and therefore have a greater combined cross sectional diameter when pressed together than is shown in FIG. 4B.

Figure 4C:
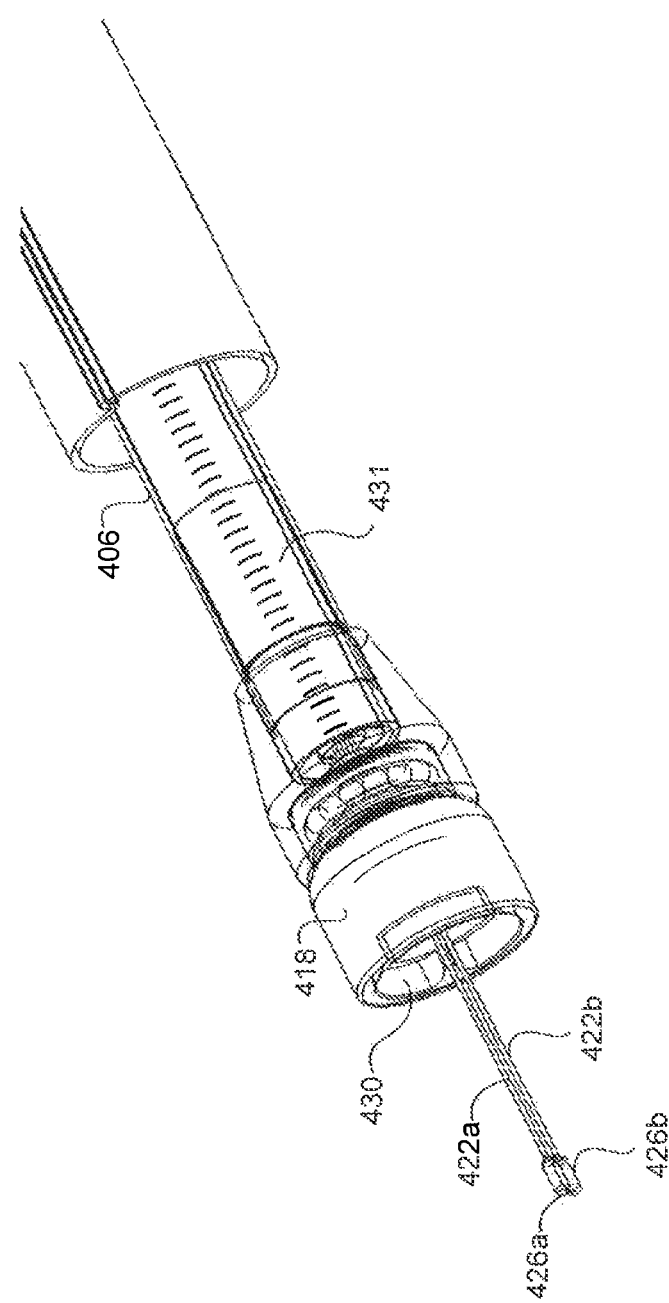
Figure 4D:
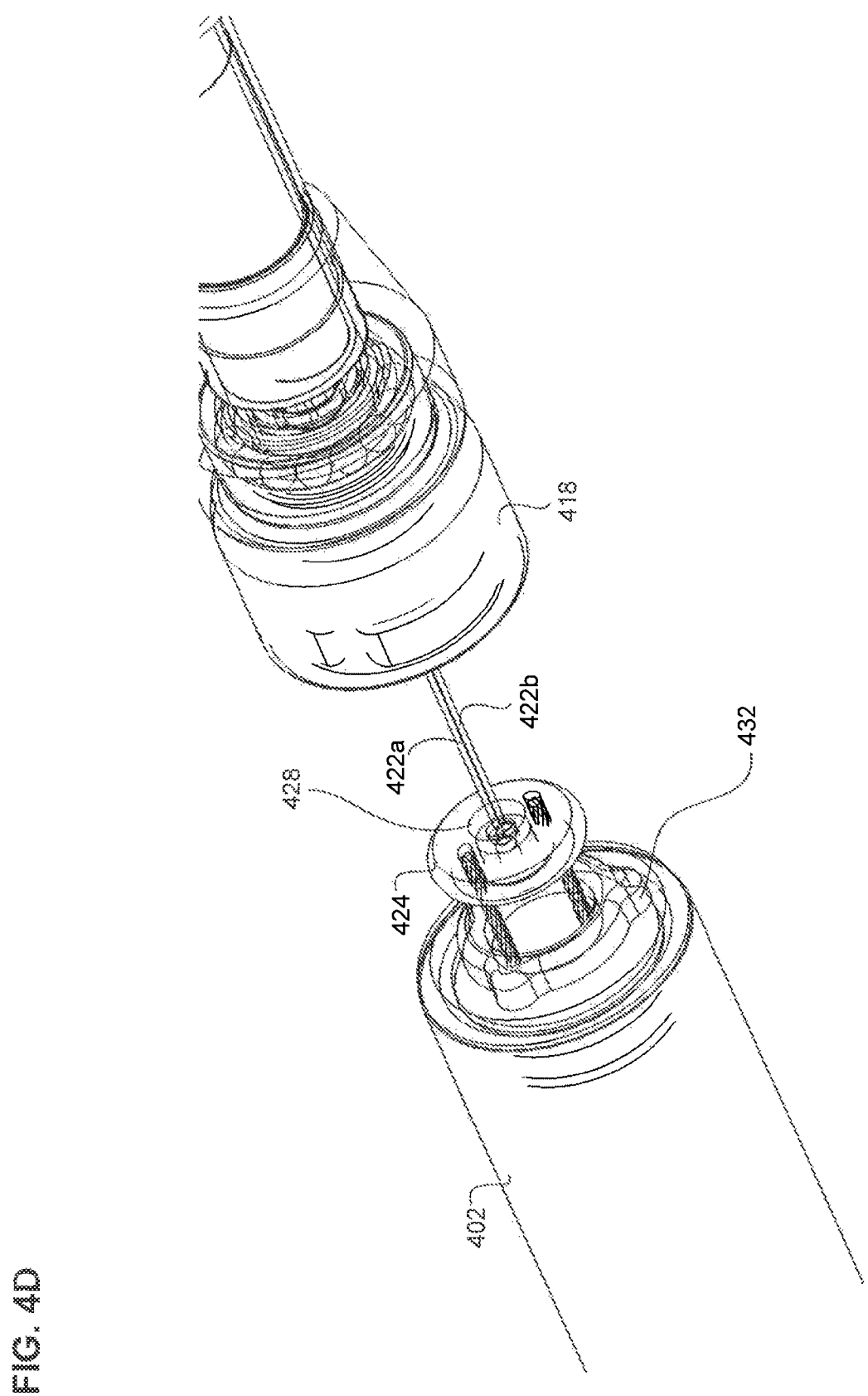
Figure 4E:
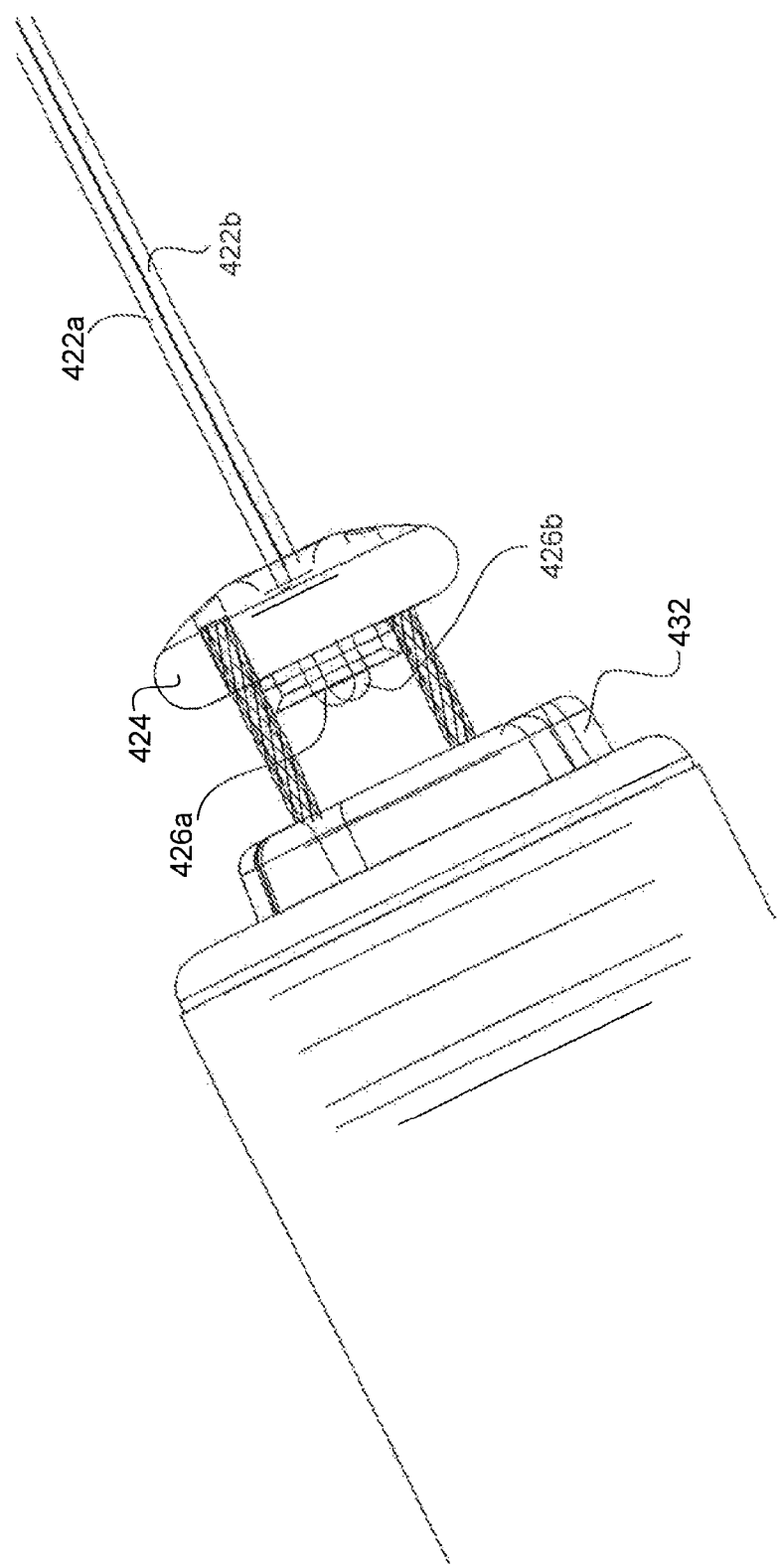
Figure 4F:
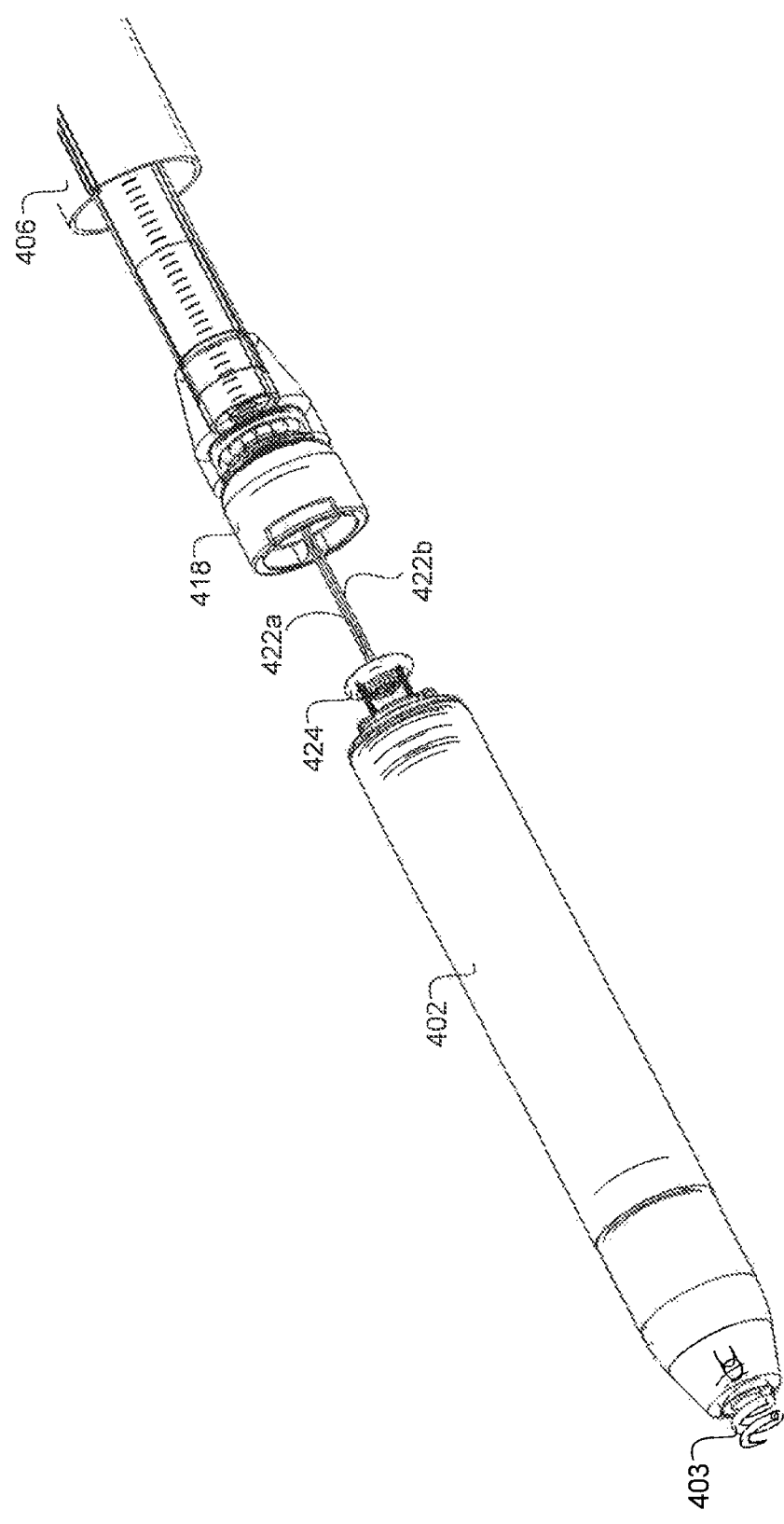

To connect the delivery catheter to the pacemaker, the length of tethers 422a and 422b, and thus the position of distal features 426a and 426b, can be adjusted so that distal features 426a and 426b are not aligned in a side by side configuration (e.g., the un-aligned configuration shown in FIGS. 4A-4B). When the tethers and distal features are in this un-aligned configuration, the cross sectional diameter of the distal features is reduced since the distal features are not positioned side by side. The tether distal features 426a and 426b can then be advanced in this un-aligned configuration through hole 428 of attachment feature 424, as shown in FIGS. 4D-4F. In this embodiment, the diameter of hole 428 should be sufficiently large enough to allow the distal features 426a and 426b of tethers 422a and 422b to pass when in the un-aligned configuration. Upon passing the distal features through the hole 428, the length of the tethers can then be adjusted to align the distal features in the side by side configuration (e.g., as shown in FIGS. 4C and 4E). When the distal features are positioned side by side, the combined cross sectional diameter of the distal features becomes larger than the diameter of hole 428, which essentially locks the tethers and distal features in the attachment feature 424 be preventing the distal features from being able to pass proximally through the hole 428.

Figure 4G:
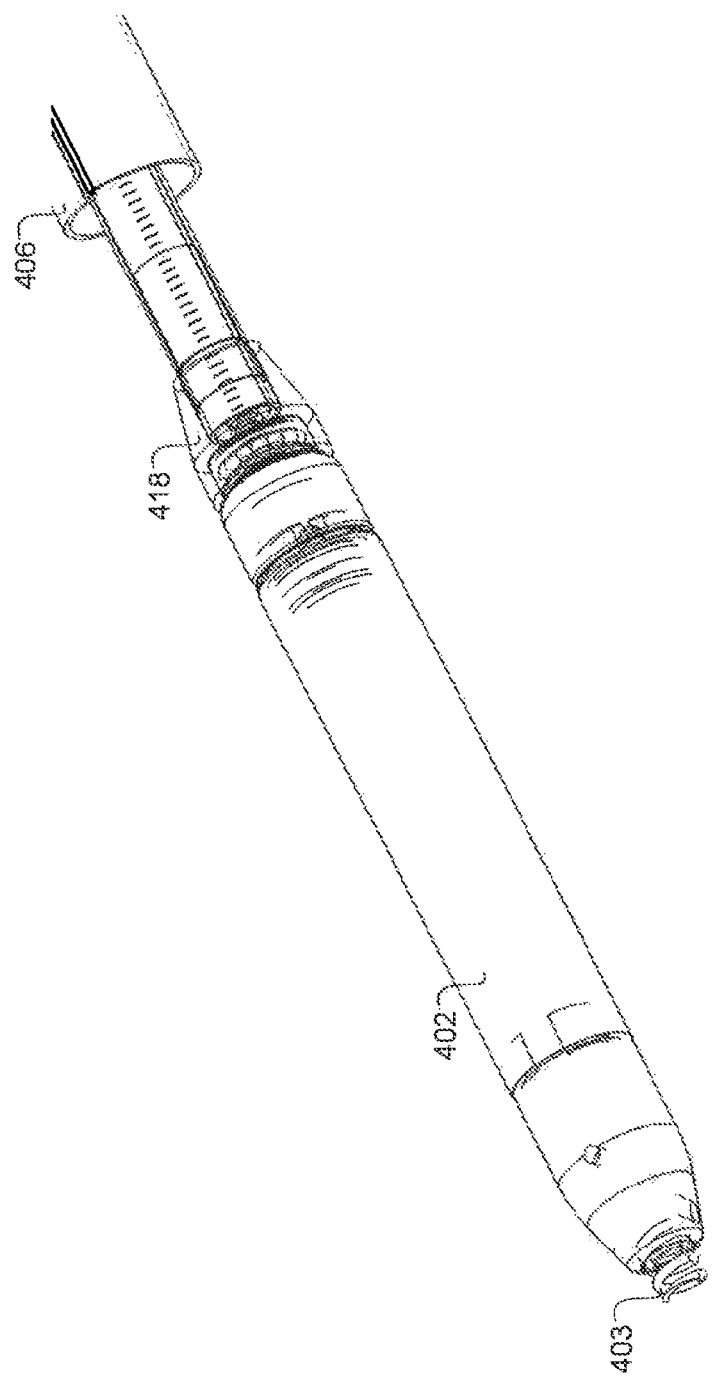

Still referring to FIGS. 4C and 4D, the docking cap 418 of the delivery catheter can include a torque slot 430 (shown in FIG. 4C) sized and configured to mate with a torque key 432 (shown in FIG. 4O) disposed on a proximal end of the pacemaker. The torque slot 430 can be coupled to a torque shaft 431, which runs the length of the delivery catheter extending into the handle (not shown). In FIGS. 4C and 4D, torque key 430 is shown as a "male" key and torque slot 430 is shown as a "female" key, but it should be understood that in other embodiments, the "male" key can be located on the attachment feature 418, and the "female" key can be disposed on the pacemaker. It should also be appreciated that key 432 and slot 430 can comprise any number of shapes, such as square, rectangle, triangle, pentagon, hexagon, cross, "X", etc, so long as key 432 fits within and can apply rotational torque to slot 430. Once the tethers are locked within the attachment feature, the tethers can be pulled proximally to pull attachment feature 424 and the pacemaker towards the catheter and to attach the pacemaker to the delivery catheter, thereby engaging torque slot 430 with torque key 432 (as shown in FIG. 4G).

Figure 5B:
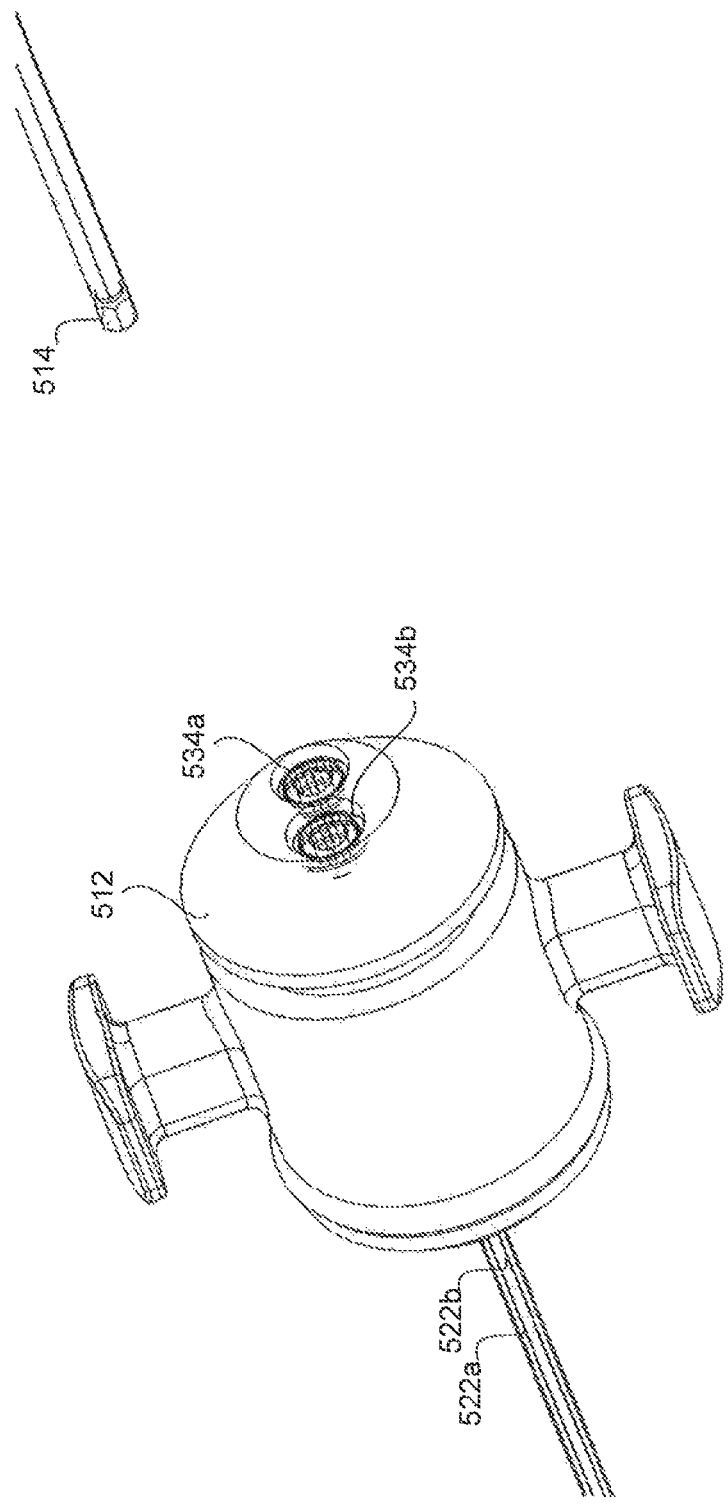

FIGS. 5A-5D are close-up views of handle 508 of delivery system 500. In FIG. 5A, handle 508 includes deflection knob 510, tether knob 512, tether adjustment feature 514, and flush ports 516. As described above, deflection knob 510 provides for steering and guidance of the catheter during implantation and/or removal of the pacemaker. The flush ports 516 can be used to flush saline or other fluids through the catheter. Referring now to FIGS. 53 and 5C, tether adjustment feature 514 can be configured to adjust then length of tethers 522a and 522b that extends distally outwards from the delivery catheter, causing the distal features (not shown) to be in either a side by side "locked" configuration or an un-aligned "unlocked" configuration.

Figure 5D:
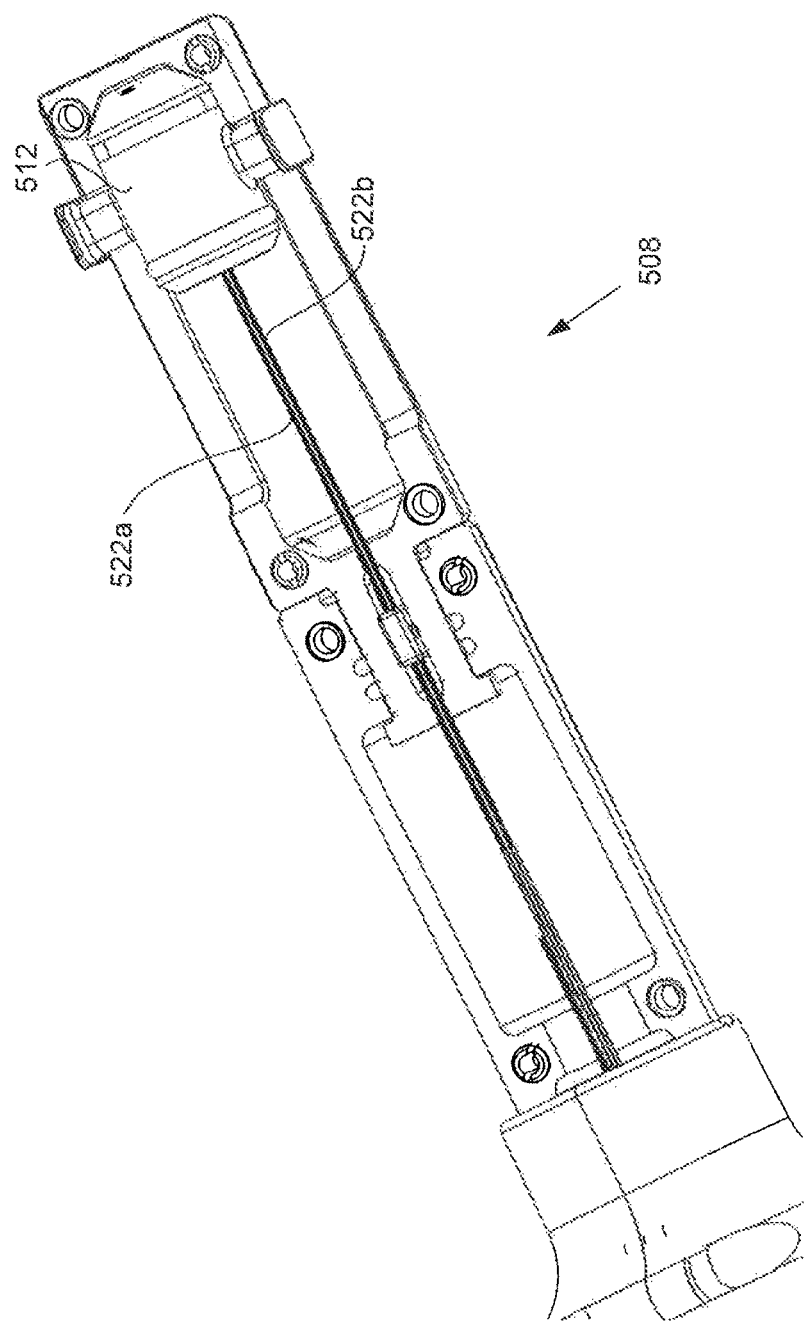

The tether adjustment feature can comprise an Allen wrench or any other suitable key, and can be configured to mate with and engage proximal keys 534a and 534b of tethers 522a and 522b, respectively, which are disposed within shuttle 512. In another embodiment, the tether adjustment feature can comprise knobs or dials on the handle itself, and a user can simply turn the knobs or dials to adjust the length of the tethers. The shuttle can be inserted into handle 508, as shown in FIG. 5D. The proximal keys 534a and 534b of tethers 522a and 522b are shown without shuttle 536 in FIG. 5C for ease of illustration. Rotation of tether adjustment feature 514 causes proximal keys 534a and/or 534b to move distally or proximally within shuttle 512, which therefore changes the length of tethers 522a and/or 522b extending distally from the delivery catheter. Thus, the tether key can be used to either align the distal features of the tethers in a side by side (e.g., locked) configuration, or alternatively, to place the distal features of the tethers in an un-aligned (e.g., unlocked configuration), permitting docking and locking of the pacemaker to the delivery catheter.

Referring back to FIGS. 4D-4G and 5A, it can now be understood how the pacemakers described herein can be delivered and attached to tissue, and then released from the delivery system. In FIGS. 40-4F, tethers 422a and 422b can be inserted in an "unlocked" or un-aligned configuration into hole 428 of attachment feature 424. The distal features of the tethers can then be aligned so as to lock the distal features in the attachment feature. Referring to FIG. 5A, tether shuttle 512 can then be pulled proximally to cause the tethers to move proximally, thereby docking the pacemaker against the delivery catheter (as shown in FIG. 4G). When the pacemaker is docked against the delivery catheter, torque key 432 of the pacemaker (shown in FIG. 4D) fits within and is mated to torque slot 420 of the delivery catheter (shown in FIG. 4C).

Referring to FIG. 5A, tether shuttle 512 of handle 508 can then be rotated, which rotates torque shaft 431 (shown in FIG. 4C) within the delivery catheter and applies torque to torque slot 430, and thus to torque key 432 on the pacemaker. By rotating the shuttle, and thus the torque shaft, the delivery catheter applies torque to the pacemaker to screw the fixation helix of the pacemaker into tissue. Once the fixation helix is fully inserted into tissue, the tethers can be placed into an un-aligned or "unlocked" configuration with tether adjustment feature 514, allowing the tethers and distal features to be removed from the attachment feature of the pacemaker. Once the delivery catheter is disengaged from the pacemaker, the catheter can be removed from the patient, leaving the pacemaker in place at the target tissue.

Figure 6A:
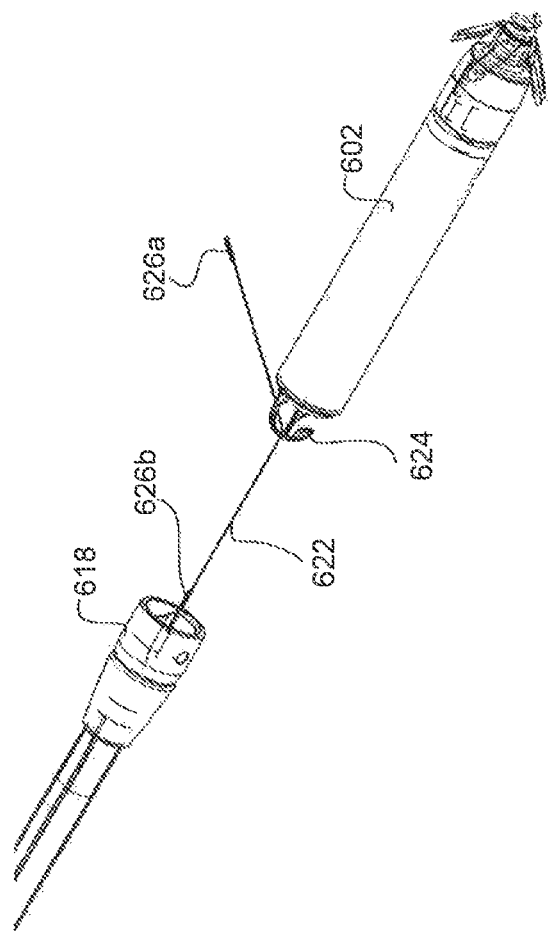
FIGS. 6A-6B are an alternate embodiment of a delivery system having a single tether.
Figure 6B:
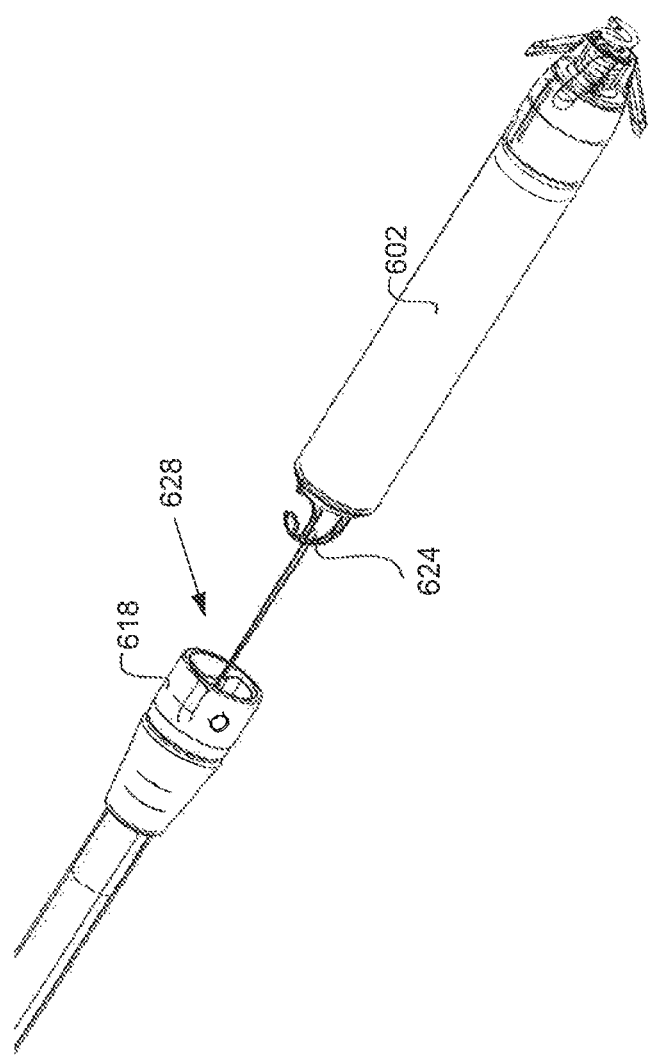

FIGS. 6A and 6B illustrate an alternate embodiment for attaching a delivery catheter to a pacemaker. The embodiment shown in FIGS. 6A and 6B employs a similar concept to that described above. However, instead of using two tethers, as described above, the embodiment of FIGS. 6A and 6B utilizes a single tether 622, having both a distal feature 626a and a proximal feature 626b. In the embodiment of FIGS. 6A and 6B, the tether 622 can comprise a shape memory alloy, such as nitinol, and can include a pre-bent or pre-biased shape. This pre-biased shape can allow the distal feature 626a of the tether to naturally bias outwards, as shown in FIG. 6A.

To attach the pacemaker 602 to the delivery catheter, as shown in FIG. 6A, the distal feature 626a of tether 622 can be threaded through attachment feature 624 of pacemaker 602. Once the tether is threaded through the attachment feature, the tether can be folded back against itself, so that distal feature 626a is adjacent to, but not directly beside proximal feature 626b. The distal and proximal features should be aligned in an un-aligned or "unlocked" configuration, as described above in the two-tether embodiments. This configuration allows the distal and proximal features to be inserted into hole 628 of docking cap 618, as shown in FIG. 6B. Once the distal and proximal features are advanced past the hole 628, an interior chamber (not shown) in the catheter opens up to a diameter larger than the diameter of the hole 628. This interior chamber has a diameter large enough to accommodate both the distal and proximal features in a side by side or "locked" configuration. Thus, the length of the tether can be adjusted to align the distal and proximal features in the side by side configuration, causing the combined cross sectional diameter of the distal and proximal features to be larger than the diameter of hole 628. The result is the locking of tether 622 within the delivery catheter.

Other features of the embodiment of FIGS. 6A-6B can be the same as described above, such as the torque keys, slots, and shafts that allow the delivery catheter to apply rotational torque to the pacemaker to screw it into tissue.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of delivering a leadless pacemaker to a patient with a delivery catheter, comprising:

positioning a first locking feature of a first tether of the delivery catheter at a longitudinal position different than that of a second locking feature of a second tether of the delivery catheter, so that a combined cross-sectional diameter of the locking features is less than a cross-sectional diameter of a hole in an attachment feature of the leadless pacemaker;

inserting the first and second locking features through the hole in the attachment feature of the leadless pacemaker; and aligning a portion of the first locking feature at the same longitudinal position than that of a portion of the second locking feature, so that the combined cross-sectional diameter of the locking features and tethers is greater than the cross-sectional diameter of the hole in the attachment feature of the leadless pacemaker.

2. The method of claim 1 further comprising pulling the leadless pacemaker proximally with the first and second tethers to place the leadless pacemaker in contact with a distal end of the delivery catheter.

3. The method of claim 1 further comprising inserting the leadless pacemaker and the delivery catheter into the patient adjacent to an implantation site, and applying rotational torque from the delivery catheter to the leadless pacemaker to screw a fixation device of the pacemaker into the implantation site.

* * * * *